(12) United States Patent
Watanabe (10) Patent No.: US 8,363,214 B2
(45) Date of Patent: Jan. 29, 2013

(54) SURFACE INSPECTION APPARATUS

(75) Inventor: Takashi Watanabe, Naka-gun (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 13/269,268

(22) Filed: Oct. 7, 2011

(65) Prior Publication Data

US 2012/0026490 A1 Feb. 2, 2012

Related U.S. Application Data

(63) Continuation of application No. 12/314,056, filed on Dec. 3, 2008, now abandoned, which is a continuation of application No. PCT/JP2007/063317, filed on Jul. 3, 2007.

(30) Foreign Application Priority Data

Jul. 4, 2006 (JP) .................................. 2006-184155

(51) Int. Cl.
*G01N 21/00* (2006.01)
(52) U.S. Cl. .................. 356/237.4; 356/237.2; 356/446
(58) Field of Classification Search .................. None
See application file for complete search history.

(56) References Cited

U.S. PATENT DOCUMENTS

| 4,831,250 | A | 5/1989 | Fukuchi et al. |
| 7,366,344 | B2 | 4/2008 | Sim |
| 7,485,858 | B1 | 2/2009 | Obara et al. |
| 2005/0280808 | A1 | 12/2005 | Backhauss et al. |
| 2007/0258085 | A1 | 11/2007 | Robbins et al. |

FOREIGN PATENT DOCUMENTS

| JP | A-6-258231 | 9/1994 |
| JP | A-11-132956 | 5/1999 |
| JP | A-11-281337 | 10/1999 |
| JP | A-2000-114329 | 4/2000 |
| JP | A-2001-4341 | 1/2001 |
| JP | A-2003-139523 | 5/2003 |
| JP | A-2006-138830 | 6/2006 |
| JP | A-2009-535782 | 10/2009 |
| WO | WO 2007/133330 A2 | 11/2007 |

OTHER PUBLICATIONS

Ann McCarthy, Color Imaging Workflow Primitives: Executives Summary, Nov. 2002, Xerox® ICC Workflow WG Scottsdale, pp. 1-12.*
Chinese Office Action issued Jul. 7, 2011 in corresponding Application No. 200780025323.4. (with English language translation).
Chinese Office Action issued May 27, 2010 in corresponding Application No. 200780025323.4. (with English language translation).
Oct. 4, 2011 Office Action issued in Japanese Patent Appln. No. 2006-184155 w/translation.
Feb. 13, 2012 Decision on Rejection issued in Chinese Patent Application No. 200780025323.4 (with translation).

* cited by examiner

*Primary Examiner* — Gregory J Toatley
*Assistant Examiner* — Juan D Valentin, II
(74) *Attorney, Agent, or Firm* — Oliff & Berridge, PLC (57) ABSTRACT

A surface inspection apparatus for observing an edge portion of an object to be inspected includes an illumination device that irradiates an illumination light to the edge portion; and an observation device that forms an image of an observation region of the edge portion illuminated with the illumination light. The illumination device emits a first irradiation beam and a second irradiation beam as the illumination light. The first irradiation beam is incident at approximately right angles to the edge portion for compensating brightness of the image and the second irradiation beam is obliquely incident laterally to the observation region of the edge portion for generating a shadow depending on a surface state of the observation region.

22 Claims, 5 Drawing Sheets

FIG.5

SURFACE INSPECTION APPARATUS

This application is a continuation of U.S. application Ser. No. 12/314,056 filed on Dec. 3, 2008 and International Application No. PCT/JP 2007/063317 filed Jul. 3, 2007.

INCORPORATION BY REFERENCE

The disclosures of the following applications are herein incorporated by reference:
Japanese Patent Application No. 2006-184155 filed Jul. 4, 2006 International Application No. PCT/JP 2007/063317 filed Jul. 3, 2007 and U.S. Continuation application Ser. No. 12/314,056 filed on Dec. 3, 2008.

BACKGROUND OF INVENTION

1. Field of the Invention

The present invention relates to a surface inspection apparatus for observing an edge portion of an object such as, for example, a semiconductor wafer or a glass substrate for a liquid crystal by irradiating a light to the edge portion.

2. Description of Related Art

In Japanese Laid-Open Patent Application No. 2003-139523, there has been proposed a surface defect inspection apparatus that irradiates a diffused light to an edge portion of a semiconductor wafer such as a silicon wafer, captures an image of the edge portion by using a plurality of CCD cameras, and inspects foreign matter or the like from the captured image.

SUMMARY OF THE INVENTION

The conventional surface defect inspection apparatus includes a C-shaped light source in the form of a letter C that irradiates a diffused light to the edge portion of a wafer from above, below, and side and three CCD cameras that capture respective images seen from above, below, and side, respectively. One of the three CCD cameras is provided opposite to a peripheral end face of the wafer. The other two CCDs are disposed in a slanted posture against a front surface and a back surface of the edge portion of the wafer. The dispositions of the light source and the CCD cameras enable the CCD cameras to efficiently receive a mirror reflection light of the light irradiated by the C-shaped light source and reflected by edge portion.

However, it is difficult for the conventional surface defect inspection apparatus to find defects and fine unevenness that occurred in the edge portion from the captured image like the surface defect inspection apparatus that captures from above an image of a wafer that is illuminated substantially right overhead.

A surface inspection apparatus for observing an edge portion of an object to be inspected according to the present invention includes: an illumination device that irradiates an illumination light to the edge portion; and an observation device that forms an image of an observation region of the edge portion illuminated with the illumination light. The illumination device is configured to emit a first irradiation beam and a second irradiation beam as the illumination light, the first irradiation beam being incident at approximately right angles to the edge portion for compensating brightness of the image and the second irradiation beam being obliquely incident laterally to the observation region of the edge portion for generating a shadow depending on a surface state of the observation region.

The illumination device may be configured so as to irradiate an illumination light having a distribution of light quantity such that a light quantity of the second irradiation beam is greater than a light quantity of the first irradiation beam. A point at which the light quantity of the second irradiation beam emitted from the illumination device is a maximum value is positioned outside a predetermined range defined in a direction from the observation region to the illumination device.

The illumination device may include a light source, and a light diffuser plate that diffuses a light irradiated from the light source from a light emission surface and irradiates it as the first and the second irradiation lights. The distribution of light quantity may be set by adjusting a relative positional relationship between the light source and the light diffuser plate. Alternatively, the distribution of light quantity may be set based on optical properties of the light diffuser plate.

The illumination device may include a first light source that generates the first irradiation beam and a second light source that generates the second irradiation beam.

It is preferred that the surface inspection apparatus further includes a moving mechanism that relatively moves the illumination device with respect to the object to be inspected.

It is preferred that in the surface inspection apparatus, the observation device may include an imaging optical system that forms an enlarge image of the observation region, and an image-capturing device that captures the enlarged image.

A light source may be used that emits a light having a bright line spectrum as the illumination light. In this case, the image-capturing device is a color image-capturing device.

The above-mentioned surface inspection apparatus can inspect the edge portion of a semiconductor wafer.

DESCRIPTION OF PREFERRED EMBODIMENTS

Figure 1:
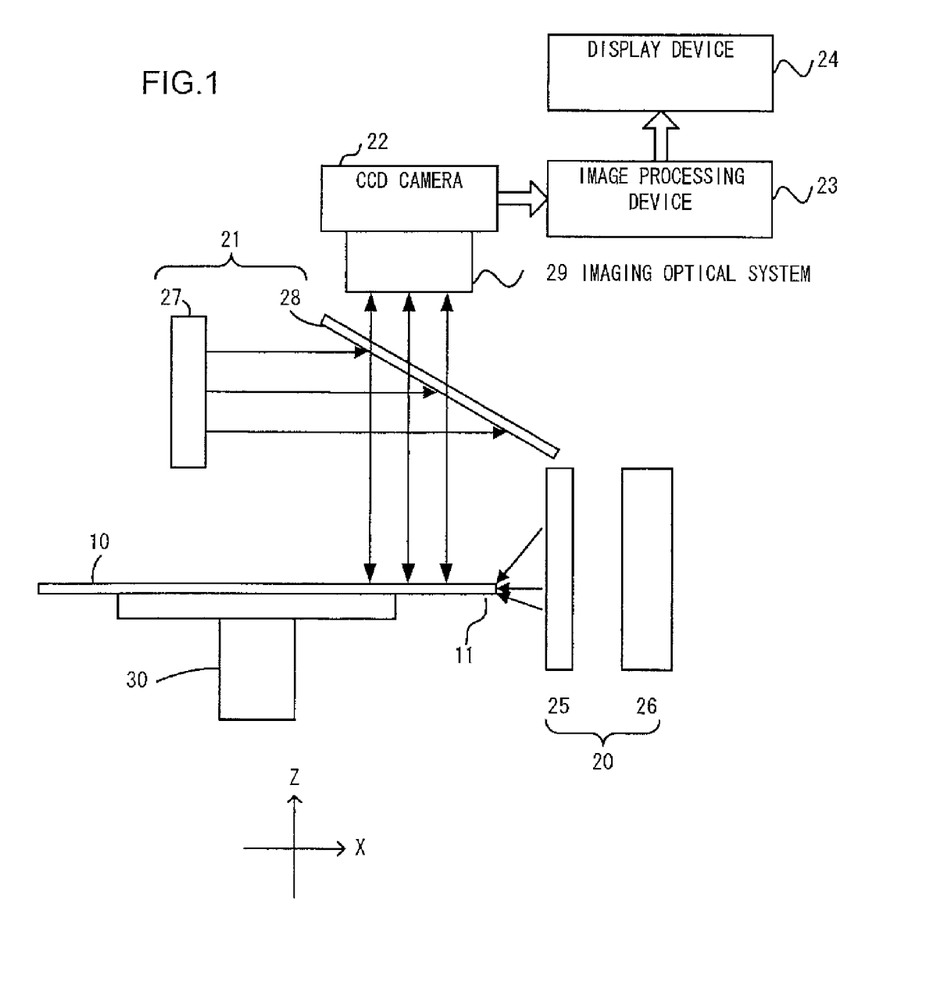
FIG. 1 is a schematic cross-section showing a surface inspection apparatus according to an embodiment of the present invention.
Figure 2:
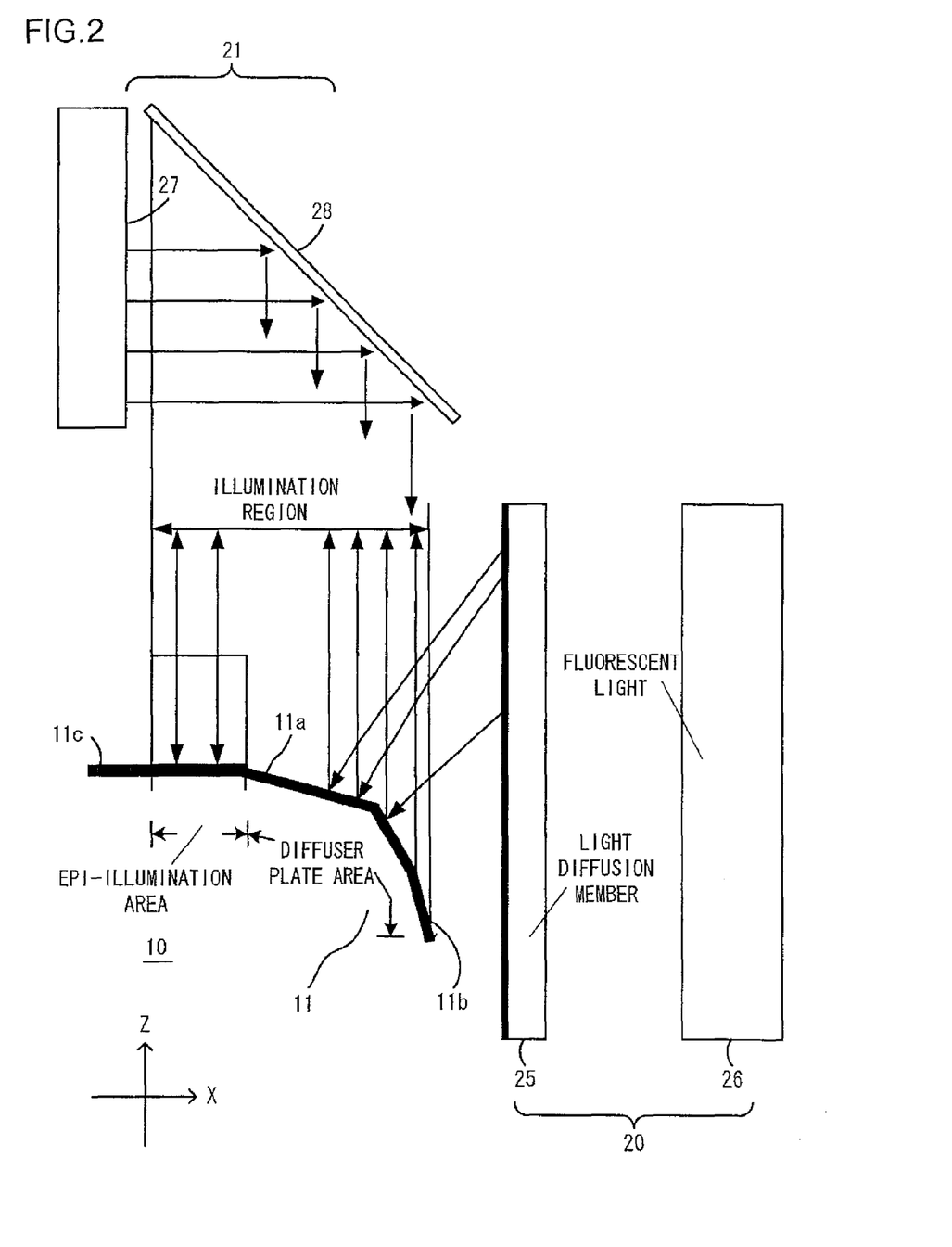
FIG. 2 is an enlarged side view showing the outline of a principal part of the surface inspection apparatus of FIG. 1.
Figure 3:
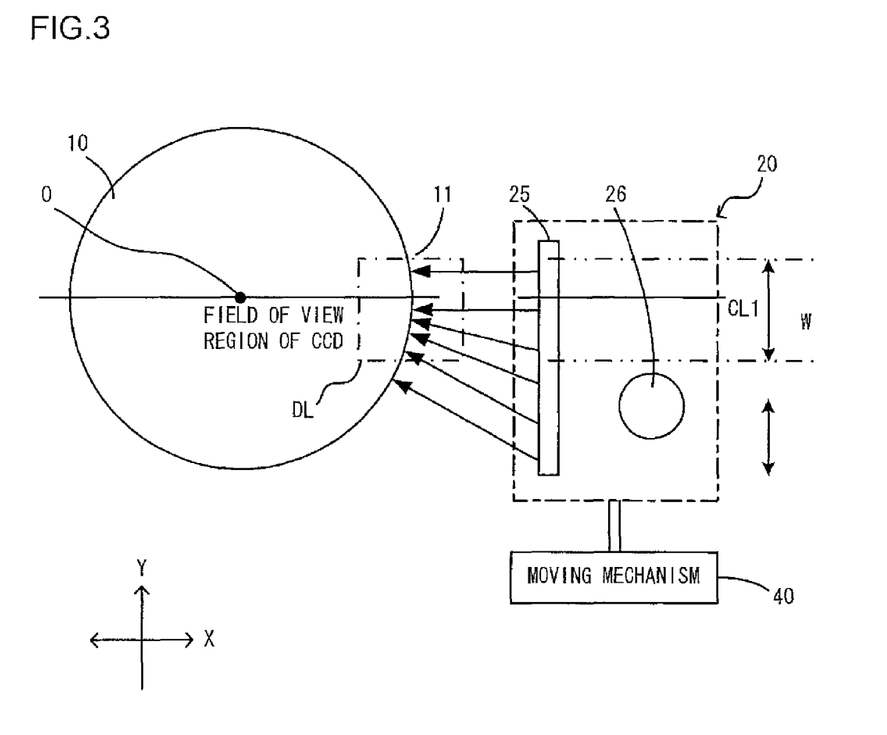
FIG. 3 is a schematic plan view of the surface inspection apparatus according to the embodiment.

The surface inspection apparatus according to an embodiment of the present invention is described with reference to FIGS. 1 to 4. The surface inspection apparatus is an apparatus that performs inspection by observing a surface of an edge portion of a silicon wafer. FIG. 1 is a schematic side view showing the surface inspection apparatus according to the embodiment of the present invention. FIG. 2 is an enlarged side view showing the outline of a principal part of the surface inspection apparatus of FIG. 1. FIG. 3 is a top view of the silicon wafer as an object of inspection and the principal portion of the surface inspection apparatus. Using an X-Y-Z coordinate system as shown in FIGS. 1 to 3, FIGS. 1 and 2 each indicate an X-Z plane and FIG. 3 indicates an X-Y plane. As shown in FIG. 2, the edge portion 11 of the silicon wafer includes a planar portion 11c that continues to a slant portion 11a and an end face portion 11b.

As shown in FIG. 1, the surface inspection apparatus includes a diffused illumination device 20, an epi-illumination device 21, a CCD camera 22, an image processing device 23, a display device 24, and an imaging optical system 29. The diffused illumination device 20 and the epi-illumination device 21 illuminate an edge portion 11 of a semiconductor wafer 10 such as a silicon wafer mounted on a turntable 30. The imaging optical system 29 forms an image of the edge portion 11 illuminated by the diffused illumination device 20 and the epi-illumination device 21 with an enlarged field of view region. The CCD camera 22 captures an enlarged image. The image processing device 23 processes the captured image signal from the CCD camera 22 to generate image data for displaying. The display device 24 displays the photographic image of the CCD camera 22 generated in the image processing device 23.

Figure 4:
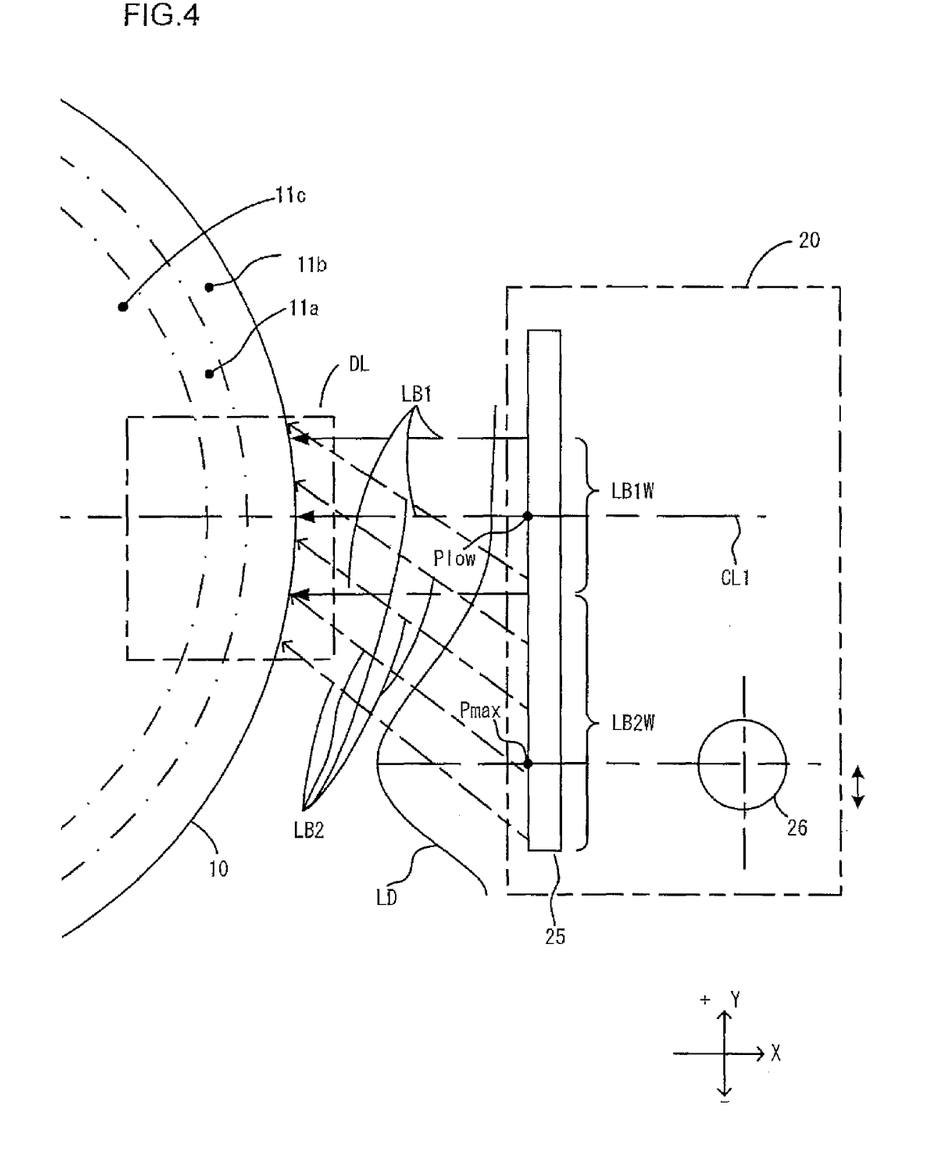
FIG. 4 is a diagram showing the distribution of light intensity of a diffuser plate.

The diffused illumination device 20 includes a light diffuser plate 25 and a fluorescent lamp 26. The illumination light from the fluorescent lamp 26 is incident to the light diffuser plate 25 to emit a diffused light from an emission surface thereof. The illumination light emitted from the diffused illumination device 20 has a distribution of light quantity. That is, it has a distribution of light intensity LD along the Y axis on the emission surface of the light diffuser plate 25 as shown in FIG. 4. In the present embodiment, the center of the fluorescent lamp 26 and the center of the light diffuser plate 25 are out of alignment one from another. The fluorescent lamp 26 is provided outside a region W defined so as to face a field of view region (field of view region of CCD) DL of the edge portion 11 laterally in the direction fronting the diffused illumination device 20. As a result, there can be obtained characteristics LD such that the light quantity is distributed along the direction of the Y axis in the light emission surface of the light diffuser plate 25 as shown in FIG. 4.

The diffused light emitted from the light diffuser plate 25 illuminates the slant portion 11a and the end face portion 11b of the edge portion 11. The diffused illumination device 20 is disposed so as to illuminate the edge portion 11 of one side (surface) of the wafer 10 obliquely from above within the X-Z plane shown in FIG. 2. The diffused illumination device 20 is disposed out of alignment below a straight line CL1 that passes a center O of the semiconductor wafer 10 in the X-Y plane shown in FIG. 3.

In FIG. 4, a predetermined region centering on a point Pmax at which the light quantity shows a peak in the direction of the Y axis of the light diffuser plate 25 is indicated by LB2W. On the other hand, a predetermined region centering on an intersection point Plow of the light diffuser plate with the center line CL1 of the wafer is indicated by LB1W. Assuming that a light incident to the edge portion 11 from the predetermined region LB1W is a first irradiation beam LB1, the first irradiation beam LB1 travels approximately in a normal direction to an outer periphery of the edge portion 11. Assuming that a light incident to the edge portion 11 from the predetermined region LB2W is a second irradiation beam LB2, the second irradiation beam LB2 is incident in an oblique direction to the outer periphery of the edge portion 11.

Note that the first irradiation beam LB1 contributes to the brightness of an enlarged image since it is reflected approximately right above at the slant portion 11a of the edge portion 11 and incident to an objective of the imaging optical system 29. In other words, the first irradiation beam LB1 compensates for the brightness of the enlarged image. On the other hand, the second irradiation beam LB2 is reflected in various directions at the slant portion 11a and does not contribute to the brightness of the enlarged image but compensates for the accuracy of inspection of defects by forming shadows behind various defects as mentioned later.

In this manner, the diffused illumination device 20 illuminates the edge portion 11 of the wafer 10 by the first irradiation beam LB1 that illuminates the outer periphery of the wafer 10 from the normal direction and by the second irradiation beam LB2 that illuminates the outer periphery of the wafer 10 in an oblique direction. Here, assuming that a plurality of observation points is lined up at predetermined intervals in the peripheral direction of the observation region DL of the edge portion 11 and a plurality of light emission points is lined up at predetermined intervals in the direction of the Y axis on the light emission surface of the light diffuser plate 25, then a plurality of lines LB2 that connect these points is defined (see FIG. 4). An angle between the line LB2 and the traveling direction of the first irradiation beam LB1 is greater toward the direction of −Y. In other words, the angle of the line LB2 increases continuously toward the direction of −Y. As a result, in the X-Y plane in FIG. 3 and FIG. 4, the edge portion 11 is illuminated from various directions, so that protrusions and depressions of various shapes can be inspected without fail.

The diffused illumination device 20 can move in the direction of the arrows shown in FIGS. 3 and 4 through a moving mechanism 40. Since the diffused illumination device 20 is moved as a unit, the distributions of the light quantity of the second irradiation beam LB2 and the light quantity of the first irradiation beam LB1 in the observation region can be adjusted by relatively shifting the distribution of light quantity LD with respect to the observation region DL. Therefore, the illumination light of the diffused illumination device 20 can be controlled such that fine protrusions and depressions occurring at the slant portion 11a or the end face portion 11b of the edge portion 11 are emphasized by shadows. For example, prior to inspection, an optimal illumination mode is determined by trials and errors.

The illumination light emitted from the fluorescent lamp 26 contains a plurality of bright line spectra (lights of various wavelengths, for example, yellow, violet, blue, and so on). Therefore, even when films of various materials are formed on the semiconductor wafer 10, there are bright line spectra that are not absorbed by the films but reflected by the films. As a result, the bright line spectra interferes with each other, so that when a plurality of films are stacked on the semiconductor wafer 10, different colors can be observed depending on the thicknesses of the films Accordingly, the surface state of the semiconductor wafer 10 can be observed as divided depending on the respective colors of the films on the wafer 10. On this occasion, the COD camera 22 is a color CCD camera.

As shown in FIG. 1, epi-illumination device 21 is disposed above the edge portion 11 of the semiconductor wafer 10. The epi-illumination device 21 causes the light from an epi-illumination light source 27 such as a halogen lamp to be reflected by a half mirror 28 to illuminate the planar portion 11c of the edge portion 11 (see FIG. 2) in the main. The imaging optical system 29 is disposed as shown in FIG. 1 such that an observation light that has been reflected by the edge portion 11 of the wafer 10 and transmitted through the half mirror 28 is incident to the imaging optical system 29 to form an enlarged image thereof. The CCD camera 22 is attached to a camera-connecting barrel of the imaging optical system 29. It captures an enlarged image and outputs an image signal.

Then, the operation of the surface inspection apparatus configured as mentioned above is described.

The semiconductor wafer 10 is mounted on the turntable 30 and rotated by the turntable 30. On this occasion, the planar portion 11c of the edge portion 11 is illuminated mainly by the epi-illumination device 21 and the slant portion 11a and the end face portion 11b are illuminated mainly by the diffused illumination device 20 as shown in FIG. 2. Among the reflected lights from the planar portion 11c, the slant portion 11a, and the end face portion 11c, the reflected light within the field of view region DL shown in FIG. 3 is transmitted through the half mirror 28 and is incident to the imaging optical system 29 to form an enlarged image with desired brightness. The enlarged image formed by the imaging optical system 29 is captured by the CCD camera 22. The enlarged image captured by the CCD camera 22 is converted into an inspection image signal, which is input into the image processing device 23 and undergoes image processing to form an inspection photographic image of the edge portion 11. The inspection photographic image is displayed on the display device 24. The CCD camera 22 performs a photographic operation repeatedly in synchronization with the rotation of the wafer 10 to take an observation image over the whole circumference of the edge portion 11. A plurality of frames of the observation images is stored in a memory not shown.

According to the surface inspection apparatus according to the above-mentioned embodiment, the following advantages are obtained.

(1) The diffused illumination device 20 is configured to emit the first irradiation beam LB1 that is incident at approximately right angles to the edge portion laterally in the observation region DL of the edge portion 11 in order to compensate for the brightness of the enlarged image and the second irradiation beam LB2 that is incident obliquely to the edge portion 11 laterally in order to generate a shadow according to a surface state of the edge portion 11 in the observation region DL. As a result, protrusions and depressions of various shapes present in the slant portion 11a and the end face portion 11b can be shaded while compensating for the brightness of the enlarged image. Therefore, the captured image signals obtained by imaging the slant portion 11a and the end face portion 11b of the edge portion 11 contain pieces of information on various protrusions and depressions, so that the edge portion of the wafer can be observed with accuracy based on the inspection photographic signals from the CCD camera 22.

(2) The illumination light from the diffused illumination device 20 is controlled such that it has a distribution of light quantity LD as shown in FIG. 4 on the light emission surface of the light diffuser plate 25 and the light quantity of the second irradiation beam LB2 that is incident obliquely to the observation region DL laterally in the edge portion 11 is made greater than the light quantity of the first irradiation beam LB1 that contributes to the brightness of the enlarged image. As a result, when there are protrusions and depressions due to adhesion of particles or protrusions and depressions due to losses occur in the slant portion 11e or the end face portion 11b, shadows of the protrusions and depressions generated on the opposite side of the diffusion illumination device 20 are sharp and dense and extend to a considerable extent particularly by the second irradiation beam LB2. Therefore, the image of protrusions and depressions captured by the CCD camera 22, image-processed by the image processing device 23, and displayed on the display device 24 is displayed as a photographic image of which even fine protrusions and depressions are easy to find since shadows are emphasized to enhance contrast.

(3) The above-mentioned first irradiation beam LB1 is a light that is incident to the semiconductor wafer 10 in an approximately normal direction to the outer circumference of the semiconductor wafer 10 and reflected thereby upwards to enter the imaging optical system 29. The second irradiation beam LB2 is a light that is incident to the outer circumference of the semiconductor wafer 10 obliquely in an approximately normal direction and is reflected to the outer circumference of the semiconductor wafer 10 and is reflected in a direction different from that of the imaging optical system 29. As a result, both a bright-field-like imaging effect and a dark-field-like imaging effect of the edge portion 11 (the slant portion 11a, the end face portion 11b) are obtained, so that not only the shadows of protrusions and depressions but also the surface state of the edge portion 11 can be observed in detail. Therefore, for example, it is possible to observe the films stacked on the surface and the edge portion 11 of the semiconductor wafer 10 to find peeling at the edge portion 11, bubbles in the films, shadow-less deposition of films, and so on.

(4) The fluorescent lamp 26 is used as a light source of the diffused illumination device 20. The fluorescent lamp 26 emits a light having a plurality of bright line spectra, so that it enables observation of the color of the edge portion 11. Since there are among the plurality of bright line spectra those bright line spectra that are not absorbed by the film and reflected thereon, the bright lines reflected on the front surface and back surface of the film interfere with each other. Therefore, the film seems in a different color depending on the thickness of the film. This enables the observation of a plurality of films on the semiconductor wafer 10 as separated by color.

The surface inspection apparatus according to the above-mentioned embodiment may be modified as follows.

(1) The illumination mode of the edge portion 11 may be modified according to anyone of (a) to (c) below depending on the defect to be inspected.

(a) It may be configured such that the distribution of light intensity on the light emission surface of the diffuser plate 24 can be varied.

(b) It may be configured such that the types of bright line spectra emitted from the fluorescent lamp 26 can be varied.

(c) It may be configured such that the duty ratio of source voltage applied to the fluorescent lamp 26 can be varied.

By achieving variation of the illumination mode as mentioned above as appropriate, that is, by switching the illumination such that the defect to be inspected can be observed without fail, it is possible to inspect the edge portion 11 under optical illumination conditions.

(2) An epi-illumination device and a CCD camera may be set also on the back side of the semiconductor wafer 10, that is, on the back side of the semiconductor wafer 10 in FIG. 1. The diffused illumination device 20 can be used for both the front and the back sides but the diffused illumination device 20 may be set on each of the front and back sides. On this occasion, also the slant portion 11e that continues to the end face portion 11b present on the back side of the semiconductor wafer 10 is irradiated with the first irradiation beam LB1 and the second irradiation beam LB2 from the diffused illumination device 20. The enlarged image in the observation region on the back side of the semiconductor wafer 10 may be formed by the imaging optical system and captured by the CCD camera.

Figure 5:
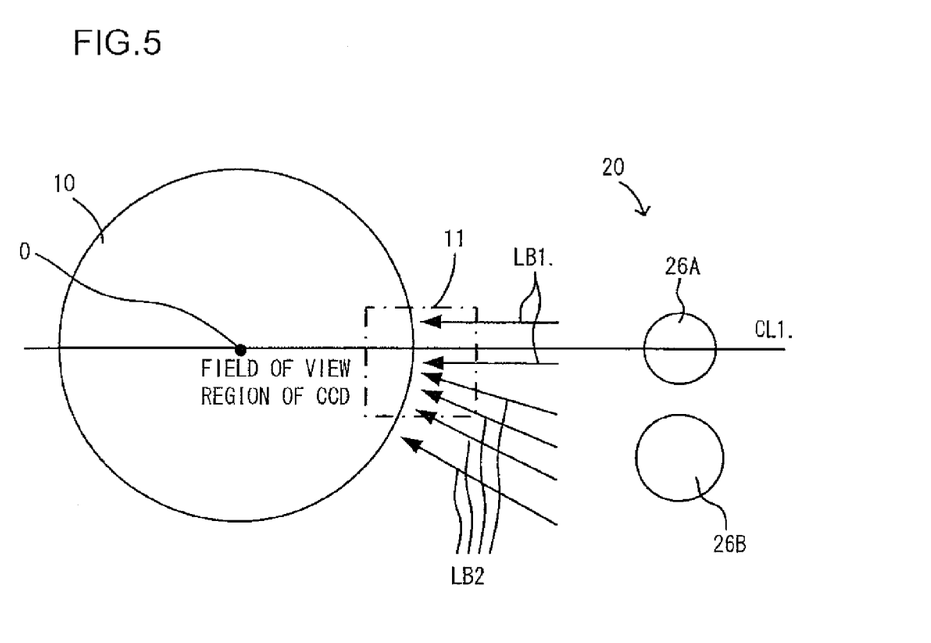
FIG. 5 is schematic plan view of a surface inspection apparatus according to a modification.

(3) Although the construction in which the light diffuser plate 25 and the fluorescent lamp 26 are configured in combination with each other as the diffused illumination device 20, the present invention is not limited thereto and the diffused illumination device 20 may be constituted by the light source alone. For example, it may be constituted by two fluorescent lamps 26. On this occasion, for example two fluorescent lamps 26A and 26B are used as shown in FIG. 5.

The fluorescent lamp 26A is disposed on the straight line L1 that passes the center of the semiconductor wafer 10 near the edge portion 11 of the semiconductor wafer 10 and the fluorescent lamp 268 is disposed at a point staggered toward a predetermined direction (downward in FIG. 5) parallel to the straight line L1. This enables illumination of the edge portion 11 with the first irradiation beam LB1 in the normal direction and the second irradiation beam LB2 at a slant with respect thereto. By setting the amount of luminescence of the fluorescent lamp 26B greater than the amount of luminescence of the fluorescent lamp 26A disposed on a line that passes the center O of the semiconductor wafer 10, the light quantity of the second irradiation beam L32 can be set to be greater than that of the first irradiation beam LB1.

(4) A solid amplifier-type image sensor, such as CMOS, may be used in place of the CCD camera 22.

(5) It may be configured such that the distribution of light quantity in the observation region is varied in the direction of the Y axis by moving the diffused illumination device 20 in the direction of the Y axis. The distribution of light intensity along the Y axis on the light emission surface of the light diffuser plate 25 can be adjusted by moving the position of the fluorescent lamp 26 with respect to the light diffuser plate 25 along the direction of the Y axis.

(6) The light diffuser plate 25 of the diffused illumination device 20 may be configured as follows. The center of the light diffuser plate 25 is made to substantially coincide with the center of axle of the fluorescent lamp 26. That is, a light having a substantially uniform distribution of light quantity is input to the light diffuser plate 25 from the fluorescent lamp 26. In addition, the optical properties of the light diffuser plate 25 are set so that the light is emitted from the light emission surface as the first and the second irradiation lights having the distribution of light quantity LD as shown in FIG. 4.

(7) The surface inspection apparatus according to the present invention can inspect edge portions of not only semiconductor wafers but also various objects to be inspected in the form of a flat plate. Other objects to be inspected include glass plates for a liquid crystal display panel and so on.

In the above description, various embodiments and modifications have been explained. However, the present invention should not be limited to the contents thereof. Other modes conceivable within the technical scope of the present invention are also included in the scope of the present invention.

What is claimed is:

1. A surface inspection apparatus for observing an edge portion of an object to be inspected, comprising:
    a first illumination device that is an epi-illumination device, the epi-illumination device includes an optical member and emits light via the optical member so as to irradiate light from above the object to at least a planar area of the edge portion;
    a second illumination device that irradiates light laterally from a side of the object to a slant area of the edge portion; and
    an observation device that captures light that is reflected by an observation region of the edge portion illuminated with the first illumination device and the second illumination device and is transmitted via the optical member, and forms an image of the observation region of the edge portion.

2. A surface inspection apparatus according to claim 1, wherein the second illumination device is configured to emit the light having at least a first portion and a second portion, wherein the first portion of the light reaching the observation region is incident at approximately right angles to at least a part of the observation region for compensating brightness of the image and the second portion of the light reaching the observation region is obliquely incident laterally to a region including at least a part of a region where the first portion of the light is irradiated in the observation region for generating a shadow depending on a surface state of the observation region.

3. A surface inspection apparatus according to claim 2, wherein:
    a light quantity, reaching the observation region, of the second portion of the light is greater than a light quantity, reaching the observation region, of the first portion of the light, wherein the light quantity represents an amount of luminescence.

4. A surface inspection apparatus according to claim 3, wherein:
    the second illumination device includes a light source and a light diffuser plate that diffuses from a light emission surface a light irradiated from the light source; and
    a position of the light source is positioned outside a predetermined range defined in a direction from the observation region to the second illumination device, a light quantity of the second portion of the light emitted from the light emission surface of the second illumination device being a maximum value at the position of the light source.

5. A surface inspection apparatus according to claim 4, wherein
    the second illumination device includes a light source and a light diffuser plate that diffuses, from a light emission surface, a light irradiated from the light source; and
    a distribution of light quantity at the light emission surface is set based on optical properties of the light diffuser plate.

6. A surface inspection apparatus according to claim 2, further comprising:
    a rotation mechanism that supports and rotates the object, wherein
    the second portion of the light is obliquely incident on a face of the object that is rotated in a rotation direction by the rotation mechanism.

7. A surface inspection apparatus according to claim 2, wherein
    the second illumination device includes a light source and a light diffuser plate that diffuses, from a light emission surface, a light irradiated from the light source; and
    a distribution of light quantity at the light emission surface is set based on a relative positional relationship between the light source and the observation region.

8. A surface inspection apparatus according to claim 1, wherein
    the second illumination device includes a first light source that generates a first portion of the light and a second light source that generates a second portion of the light.

9. A surface inspection apparatus according to claim 1, further comprising:
    a moving mechanism that relatively moves the second illumination device with respect to the object to be inspected.

10. A surface inspection apparatus according to claim 1, wherein
    the observation device includes an imaging optical system that forms an enlarged image of the observation region, and an image-capturing device that captures the enlarged image.

11. A surface inspection apparatus according to claim 10, wherein
the light irradiated with the second illumination device has a bright line spectrum and the image-capturing device is a color image-capturing device.

12. A surface inspection apparatus according to claim 1, wherein
the light irradiated with the second illumination device has a bright line spectrum.

13. A surface inspection apparatus according to claim 1, wherein
the object to be inspected is a semiconductor wafer.

14. A surface inspection apparatus according to claim 1, wherein the first illumination device is disposed above a top portion of the edge portion.

15. A surface inspection apparatus according to claim 1, wherein the second illumination device includes a light source and a light diffuser plate that diffuses a light irradiated from the light source.

16. A surface inspection apparatus according to claim 1, wherein:
the epi-illumination device further includes an epi-illumination light source; and
the optical member reflects light from the epi-illumination light source and transmits light that is reflected by an observation region of the edge portion illuminated with the first illumination device and the second illumination device.

17. A surface inspection apparatus for observing an edge portion of an object to be inspected, comprising:
a first illumination device that is an epi-illumination device, the epi-illumination device includes an optical member and emits light via the optical member so as to irradiate light from above the object;
a second illumination device that irradiates light laterally from a side of the object to the edge portion that includes an area illuminated with the first illumination device; and
an observation device that captures light that is reflected by an observation region of the edge portion illuminated with the first illumination device and the second illumination device and is transmitted via the optical member, and forms an image of the observation region of the edge portion.

18. A surface inspection apparatus according to claim 17, wherein the second illumination device is configured to emit light having at least a first portion and a second portion, wherein the first portion of the light reaching the observation region has a bright-field-like imaging effect when observing the observation region and the second portion of the light is obliquely incident to a region including at least a part of a region where the first portion of the light is irradiated and having a dark-field-like imaging effect when observing the observation region.

19. A surface inspection apparatus according to claim 18, wherein
the second illumination device includes a light source and a light diffuser plate that diffuses from a light emission surface a light irradiated from the light source.

20. A surface inspection apparatus according to claim 19, wherein
a position of the light source is positioned outside a predetermined range defined in a direction from the observation region to the second illumination device, a light quantity of the second portion of the light emitted from the light emission surface of the second illumination device being a maximum value, wherein the light quantity represents an amount of luminescence at the position of the light source.

21. A surface inspection apparatus according to claim 17, wherein:
the epi-illumination device further includes an epi-illumination light source; and
the optical member reflects light from the epi-illumination light source and transmits light that is reflected by an observation region of the edge portion illuminated with the first illumination device and the second illumination device.

22. A surface inspection apparatus for observing an edge portion of a flat plate object, the edge portion having at least an upper surface portion, a slant portion and an end portion, comprising:
a first illumination device that includes an epi-illumination device and an optical member, the epi-illumination device emits light and the optical member reflects the light from the epi-illumination device so as to irradiate the reflected light to a part of the upper surface portion included in the edge portion from above the flat plate object;
a second illumination device that includes a light source and a light diffuser plate, the light diffuser plate diffusing light from the light source and irradiating the diffused light to the upper surface portion and the end portion included in the edge portion laterally from above the flat plate object and laterally from a side the flat plate object; and
an observation device that captures light that is reflected by the edge portion illuminated with the first illumination device and the second illumination device and is transmitted through the optical member, and forms an image of the edge portion of the flat plate object.

* * * * *